(12) United States Patent
de Bie et al.

(10) Patent No.: US 11,694,811 B2
(45) Date of Patent: Jul. 4, 2023

(54) VITAL SIGN MONITORS FOR INPATIENT MEDICINE WARDS

(71) Applicant: Hill-Rom Services, Inc., Batesville, IN (US)

(72) Inventors: Johannes de Bie, Monte San Pietro (IT); Yuan Shi, Singapore (SG)

(73) Assignee: Hill-Rom Services, Inc., Batesville, IN (US)

( * ) Notice: Subject to any disclaimer, the term of this patent is extended or adjusted under 35 U.S.C. 154(b) by 417 days.

(21) Appl. No.: 16/918,904

(22) Filed: Jul. 1, 2020

(65) Prior Publication Data

US 2021/0005323 A1 Jan. 7, 2021

Related U.S. Application Data

(60) Provisional application No. 62/870,967, filed on Jul. 5, 2019.

(51) Int. Cl.
  *G16H 50/30* (2018.01)
  *A61B 5/0205* (2006.01)
  *A61B 5/00* (2006.01)

(52) U.S. Cl.
  CPC ......... *G16H 50/30* (2018.01); *A61B 5/02055* (2013.01); *A61B 5/7275* (2013.01);
  (Continued)

(58) Field of Classification Search
  CPC .. G16H 50/30; A61B 5/02055; A61B 5/7275; A61B 5/7405; A61B 5/742; A61B 5/746; A61B 2505/03; A61B 5/002; A61B 5/0205; A61B 5/4857; A61B 5/01; A61B 5/14532; A61B 5/14542
  See application file for complete search history.

(56) References Cited

U.S. PATENT DOCUMENTS 4,129,125 A 12/1978 Lester et al.
7,946,995 B1 * 5/2011 Koh ..................... A61B 5/0205
                                                     600/513
(Continued)

FOREIGN PATENT DOCUMENTS

WO    WO2019018879 A1    1/2019

OTHER PUBLICATIONS

Davoudi, A., Malhotra, K.R., Shickel, B. et al. Intelligent ICU for Autonomous Patient Monitoring Using Pervasive Sensing and Deep Learning. Sci Rep 9, 8020 (2019). https://doi.org/10.1038/s41598-019-44004-w (Year: 2019).*

(Continued)

*Primary Examiner* — Eric F Winakur
*Assistant Examiner* — Elina Sohyun Ahn
(74) *Attorney, Agent, or Firm* — Lee & Hayes, P.C.

(57) ABSTRACT

Systems and methods for vital sign monitors are disclosed herein. In some cases, a warning score is calculated based on first measurements of a first biological condition and second measurements of a second biological condition. In particular cases, the first measurements and the second measurements are automatically measured during the same time period. The warning score may be calculated based on an average of the first measurements and an average of the second measurements. Based on determining that the warning score is outside of a predetermined range, a clinical device may output an alert.

18 Claims, 11 Drawing Sheets

(52) U.S. Cl.
CPC ............ *A61B 5/742* (2013.01); *A61B 5/7405* (2013.01); *A61B 5/746* (2013.01); *A61B 2505/03* (2013.01)

(56) References Cited

U.S. PATENT DOCUMENTS

| | | | |
|---|---|---|---|
| 8,491,492 B2 | 7/2013 | Shinar et al. | |
| 8,602,997 B2 | 12/2013 | Banet et al. | |
| 8,823,527 B2 | 9/2014 | Husen et al. | |
| 10,068,461 B2 | 9/2018 | Wildman et al. | |
| 11,147,476 B2 * | 10/2021 | Shinar | A61B 5/4815 |
| 2008/0162182 A1 | 7/2008 | Cazares et al. | |
| 2009/0192751 A1 * | 7/2009 | Kamath | A61B 5/1477 |
| | | | 73/1.02 |
| 2009/0299767 A1 * | 12/2009 | Michon | G16H 10/60 |
| | | | 707/999.005 |
| 2014/0200691 A1 * | 7/2014 | Lee | A61B 5/681 |
| | | | 700/91 |
| 2016/0071393 A1 * | 3/2016 | Kaplan | A61B 5/162 |
| | | | 340/539.12 |
| 2016/0302671 A1 * | 10/2016 | Shariff | A61B 5/7246 |
| 2018/0272066 A1 | 9/2018 | McMahon et al. | |
| 2018/0303434 A1 | 10/2018 | Selvaraj | |
| 2020/0170566 A1 * | 6/2020 | Radivojevic | A61B 7/04 |

OTHER PUBLICATIONS

Merriam-Webster, (n.d.). Pager definition & meaning. Merriam-Webster. Retrieved Sep. 29, 2022, from https://www.merriam-webster.com/dictionary/pager (Year: 2022).*

The Extended European Search Report dated Nov. 11, 2020 for European Patent Application No. 20183731.7 a foreign counterpart of U.S. Appl. No. 16/918,904, 9 pages.

Smith et al., "Hospital-wide physiological surveillance—A new approach to the early identification and management of the sick patient", Resuscitation, vol. 71, No. 1, Elsevier, Oct. 2006, pp. 19-28.

Churpek et al., "The value of vital sign trends for detecting clinical deterioration on the wards," Resuscitation, vol. 102, May 2016, pp. 1-14.

* cited by examiner

| Patient | Warning Score | Circadian Variation | Status |
|---|---|---|---|
| First Individual | 2 | 1 | Normal |
| . | . | . | . |
| . | . | . | . |
| . | . | . | . |
| Nth Individual | 7 | 5 | ALERT |

CLINICAL DEVICE 202

VITAL SIGN MONITORS FOR INPATIENT MEDICINE WARDS

CROSS-REFERENCE TO RELATED APPLICATION

This application claims the benefit of U.S. Provisional Application No. 62/870,967, filed on Jul. 5, 2019, which is hereby incorporated by reference in its entirety.

BACKGROUND

In inpatient clinical environments outside of an Intensive Care Unit (ICU), a single care provider may be responsible for monitoring multiple patients. In some cases, the care provider may actively measure vital signs of the patients and compare the vital signs to predetermined ranges that are consistent with healthy individuals. When a patient's vital signs are outside of normal ranges, the care provider may initiate additional medical treatment for the patient. For instance, the vital signs may indicate that the patient requires critical care, and the care provider may transfer the patient to an ICU. In the ICU, the patient may be monitored continuously by a devoted care provider.

However, as the number of patients that the care provider is responsible for increases, the care provider may measure vital signs less frequently. In non-emergency conditions, a care provider may measure a patient's vital signs once every eight hours, in some cases. Although measuring the patient's vital signs at this frequency can enable the care provider to monitor other patients as well, a patient's condition may deteriorate rapidly between the eight-hour sampling period. As a result, the care provider may be less likely to catch early signs of patient deterioration, and the care provider may be unable to initiate early interventions for a deteriorating patient.

Automated sensors configured to automatically determine patient vital signs can assist care providers with large patient caseloads. Unlike manual vital sign measurements, automated sensors can measure a patient's vital signs without the presence or intervention of the care provider. However, the quality of vital sign determinations made by automated sensors can be significantly lower than the quality of vital sign measurements taken directly by care providers. For instance, in cases of measuring heart rate measurements, automated sensors may measure a patient's heart rate regardless of the patient's physical position or sensor placement. In contrast, a care provider may ensure that a patient is in a relaxed physical position and that the placement of sensors is ideal before measuring the patient's heart rate. Accordingly, some measurements measured by automated sensors are more likely to be inaccurate than measurements measured directly by care providers.

In some cases, automated sensors can measure vital signs semi-continuously, such as once every minute. However, these measurements may have a significant amount of noise. When the care provider is notified of every measurement that deviates from a particular threshold, the noise in the measurements may increase the risk that a care provider may be called to a patient's bedside when the patient is not in distress. The noise may also increase the risk that a care provider is not notified when the patient is in distress. These risks are further exacerbated by natural vital sign variations between healthy patients, natural vital sign variations throughout the day of a single healthy patient, and relatively low-quality measurements inherent in automated sensors.

DESCRIPTION OF THE FIGURES

The following figures, which form a part of this disclosure, are illustrative of described technology and are not meant to limit the scope of the claims in any manner.

DETAILED DESCRIPTION

Figure 1:
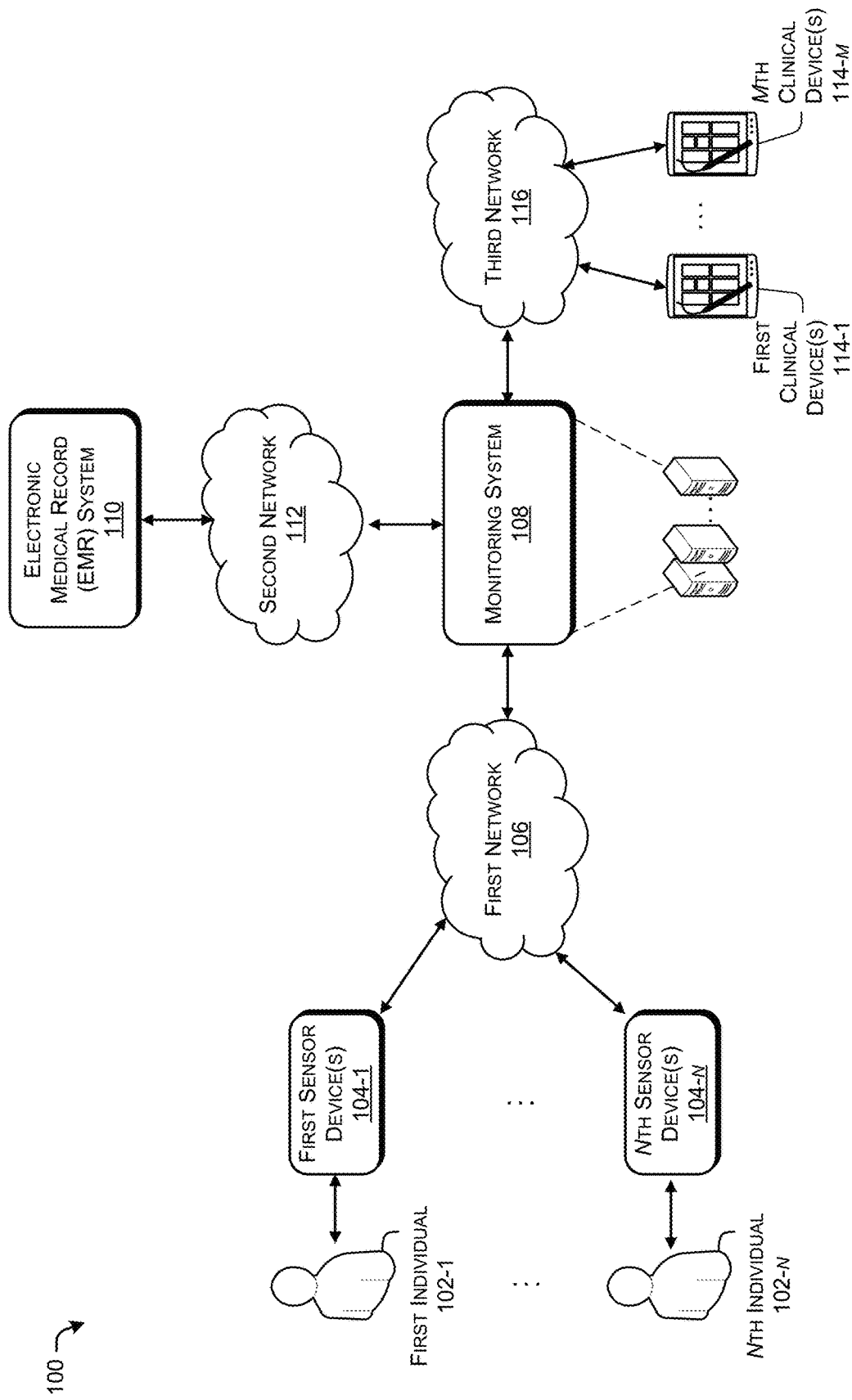
FIG. 1 illustrates an example environment for continuously monitoring vital signs of multiple patients.

Various implementations of the present disclosure will be described in detail with reference to the drawings, wherein like reference numerals present like parts and assemblies throughout the several views. Additionally, any samples set forth in this specification are not intended to be limiting and merely set forth some of the many possible implementations.

The present disclosure provides various devices, systems, and methods for monitoring vital signs and other biological conditions of patients. In some cases, a patient's vital signs are measured by automated sensors over a time period (e.g., an hour) and only an average vital sign measurement over the time period may be reported to a device operated by a care provider. In some cases, corrections can be applied to the average based on a trend of the patient's vital signs over the course of the time period. Accordingly, the care provider can be undistracted by short-term variations in the measurements determined by the automated sensors.

In certain implementations, a warning score may be determined based on a patient's average vital signs. The warning score can be an early warning score (e.g., a National Early Warning Score (NEWS)), or similar value, that combines multiple vital signs into a single metric that can be used to assess whether a patient's condition may be deteriorating or may be likely to deteriorate. The warning score can further simplify the information provided to the care provider, so that the care provider can assess a patient's condition based on a single value rather than multiple vital signs.

A patient's vital signs, warning score, and other health indicators can vary periodically over a 24-hour period, but may also be associated with an offset when the periodic variance is removed. As used herein, the term "circadian offset" can refer to a change in a health indicator separated by a period of about 24 hours. A circadian offset can therefore remove the variations of the health indicator due to a patient's circadian rhythm.

In some cases, a patient's current vital signs and/or warning score are compared to previously stored vital signs and/or warning score that were determined approximately 24 hours prior. For instance, a patient's average vital sign for the past hour can be compared to an average vital sign of the patient determined approximately 24 hours ago. In some cases, a first average of a vital sign may be generated by averaging measurements in a first time period and a second average of a vital sign may be generated by averaging measurements in a second time period, where the second time period is, at least in part, 24 hours after the first time period. To reduce the impacts of changes in the measurements determined during first time period on the circadian offset, in certain implementations, the first time period may be longer than the second time period. In some cases, the patient's circadian offset may also be reported to the device operated by the care provider. The circadian offset can provide an additional metric that the care provider can use to determine whether the patient may require critical care intervention. A patient that requires critical care intervention may require transfer to an ICU.

In certain cases, a care provider may be alerted when a patient's average vital signs, warning score, and/or circadian offset are determined to be abnormal (e.g., outside of at least one normal range) or otherwise indicate that the patient may be likely to require critical care intervention. Because the average vital sign reduces the impacts of short-term variations in the measurements determined by the automated sensors, the average vital sign can further enhance the specificity of alerts provided when the patient's vital signs, warning score, and/or circadian offset are outside of normal ranges. In some cases, the alert may be triggered only if multiple metrics (e.g., a vital sign and the circadian offset, multiple vital signs, the warning score and the circadian offset, etc.) are determined to be abnormal. In these cases, the specificity of the alert may be further enhanced.

The term "normal range," as used herein, can refer to a range of a metric that is associated with a relatively low likelihood of disease or medical complications. In various examples, a normal range can be predetermined. In some cases, a normal range is defined according to a government authority (e.g., an agency designed to promote public health, such as the Center for Disease Control (CDC) in the United States), according to an academic authority (e.g., a medical school), or the like. In some cases, a normal range can be determined based on machine learning. For instance, one or more neural networks may be trained to identify whether an individual is likely (e.g., over 75% likely) to require critical care based on one or more vital signs.

In various implementations, information about the patient (e.g., average vital signs, warning scores, and/or circadian offsets) can be selectively reported to a clinical device. In some cases, significant information about multiple patients can be displayed on a single user interface output by the device. The information output reported to the device and output by the device can enable a single care provider to manage multiple patients in a hospital environment. In some cases, the device may selectively output average vital signs, a warning score, and/or a circadian offset for each of multiple patients on the same screen. The average vital sign may be averaged over a previous hour and may be labeled an "hourly vital sign." The circadian offset may be labeled a "change since yesterday." In particular examples, the device may selectively output an alert corresponding to any of the multiple patients whose average vital signs deviate from normal ranges, whose warning score deviates from a normal range, and/or whose circadian offset deviates from a normal range. In certain cases, the device may refrain from outputting individual vital sign measurements determined by automatic sensors. Accordingly, the device may provide an efficient and easy-to-use user interface for providers monitoring multiple patients in a hospital environment. In particular examples, the device may be used to effectively monitor multiple patients in a ward environment. The device can be used by clinicians to determine whether patients should be transferred to an ICU for more continuous monitoring, in some cases.

Various implementations of the present disclosure provide improvements to the technical field of semi-continuous healthcare monitoring systems. By providing and assessing patient conditions based on running averages, short-term noise can be ignored and false positives can be avoided. As a result, certain implementations of the present disclosure enhance the specificity of systems that semi-continuously monitor biological conditions of patients.

Furthermore, by providing and assessing patient conditions based on circadian offsets, alerts can be avoided based on healthy periodic variations in patient conditions occurring throughout 24-hour periods. Accordingly, the sensitivity and specificity of systems that continuously monitor biological conditions of patients can be further enhanced.

Particular user interfaces and reporting systems disclosed herein can also improve monitoring systems. By providing clinically relevant information to a user device of a care provider, the care provider can remotely monitor a patient's condition. In addition, by providing rapid and targeted alerts with high sensitivity and specificity, the care provider can efficiently identify and intervene when a patient requires additional medical attention. Furthermore, by providing a user interface that allows the care provider to monitor the conditions of multiple patients at once, the care provider can effectively provide high-quality care to a relatively large number of patients. Various implementations of the present disclosure can have practical applications to the fields of medical devices and healthcare management. Particular implementations will be discussed below with respect to the accompanying figures.

FIG. 1 illustrates an example environment 100 for continuously monitoring vital signs of multiple patients. The example environment 100 can be associated with a healthcare facility, in some cases. As shown with respect to at least FIG. 1, first through nth individuals 102-1 to 102-$n$ can be monitored by first through nth sensor devices 104-1 to 104-$n$, wherein n is a positive integer. As used herein, the terms "individual," "patient," and their equivalents, can refer to a person who may be being actively monitored by a healthcare facility. In particular implementations, the individuals 102-1 to 102-$n$ can be individuals residing at least temporarily in a healthcare facility. For instance, the first individual 102-1 may be an individual who may be being monitored after a surgical procedure. In some implementations, the individuals 102-1 to 102-$n$ may be monitored outside of an ICU or other environment providing constant care and oversight from healthcare providers. For instance, the individuals 102-1 to 102-$n$ may be monitored in medical wards.

The sensor devices 104-1 to 104-$n$ may include sensors that measure, sense, detect, and/or otherwise determine various conditions of the individuals 102-1 to 102-$n$. As used herein, the terms "sensor," "biological sensor," "vital sign sensor," and their equivalents, can refer to a device configured to measure, sense, detect, and/or otherwise determine a biological condition of an individual. As used herein, the terms "biological condition," "condition," and their equivalents, can refer to a physical parameter of an individual's body or a metric based on a physical measurement of the individual's body. In some examples a biological condition can be a vital sign (e.g., blood pressure, heart rate, temperature, respiration rate, blood oxygen saturation, etc.).

In some cases, sensors can further report the measured biological conditions to one or more external devices. Some examples of sensors include pressure sensors, blood-pressure sensors, heart rate sensors, body temperature sensors, respiratory rate sensors, end-tidal $CO_2$ sensors, blood oxygen saturation sensors (e.g., pulse oximeters and/or other sensors that measure peripheral oxygen saturation ($SpO_2$) oxygen saturation in arterial blood), chemical sensors (e.g., glucose sensors), electrical sensors (e.g., Electrocardiogram (ECG) sensors, Electroencephalogram (EEG) sensors, etc.), consciousness sensors (e.g., devices prompting individuals to engage in interactive mental exercises) and the like.

According to some implementations, the sensor devices 104-1 to 104-n can measure the conditions multiple times in a time interval. In some cases, the sensor devices 104-1 to 104-n can sample the conditions semi-continuously or periodically. As used herein, the term "semi-continuously" can mean something that may be performed at a sampling rate that meets or exceeds a minimum sampling rate defined according to the Nyquist theorem. In some examples, any one of the sensor devices 104-1 to 104-n may have a sampling rate of approximately 1-100 samples per minute, approximately 1-100 samples per hour, approximately 1-100 samples per day, or the like.

The sensor devices 104-1 to 104-n can transmit data indicating the measurements over a first network 106 to a monitoring system 108. In some cases, the sensor devices 104-1 to 104-n can measure various parameters (e.g., pressure, temperature, pulse frequency, electrical signals, etc.) associated with the individuals 102-1 to 102-n, generate signals indicating the measurements based on the parameters, and transmit the signals to the monitoring system 108. In some cases, the measurements can be derived by the sensor devices 104-1 to 104-n and/or the monitoring system 108 based on the parameters. As used herein, the term "network," and its equivalents can refer to any suitable communication network by which multiple nodes can exchange data. Examples of networks include Wide Area Networks (WANs), such as the Internet; Personal Area Networks (PANs); Local-Area Networks (LANs), Metropolitan-Area Networks (MANs), and the like. Networks can be wireless, such that nodes can communicate with each other over one or more wireless protocols, such as WLAN, WI-FI™, BLUETOOTH™ and the like. In some cases, nodes can exchange data in the form of one or more data packets. For example, the sensor devices 104-1 to 104-n can generate data packets by packaging the data indicating the measurements into data packets and transmit the data packets to the monitoring system 108 over the first network 106.

The monitoring system 108 may be configured to analyze the measurements and selectively report indications of the measurements. According to various implementations, the monitoring system 108 may time-average measurements and report the averages. In some examples, the monitoring system 108 may refrain from reporting every one of the measurements. For instance, the monitoring system 108 may identify multiple measurements of the first individual's 102-1 blood pressure determined over the course of a time period (e.g., one hour), determine an average of the first individual's 102-1 blood pressure over the time period, and report the average without reporting each of the measurements.

The monitoring system 108 may determine and apply corrections to the averages based on identified trends in the measurements. In particular implementations, the monitoring system 108 may determine a linear line-of-best-fit (e.g., a "trend line") for multiple measurements determined over the course of the time period. The monitoring system 108 can determine the linear line-of-best-fit by performing linear regression on the multiple measurements. In some implementations, the monitoring system 108 may report a value on the linear line-of-best-fit. For instance, the monitoring system 108 may identify multiple measurements of the first individual's 102-1 blood pressure determined over the course of a time period (e.g., one hour), determine a linear line-of-best-fit by performing linear regression on the measurements, and determine an estimated value of the individual's blood pressure at the end of the time period to be a value of the line-of-best-fit corresponding to the end of the time period. The linear regression may be performed with the assumptions of weak exogeneity of the time variable, linearity of the measurements over time, constant variance among the measurements, independence of errors within the measurements, and lack of perfect multicollinearity.

In some implementations, the monitoring system 108 may correct the average measurement based on the line-of-best fit. For instance, the monitoring system 108 may assume that the average measurement may be an estimated measurement halfway through the time period and use the line-of-best-fit to interpolate a corrected estimate for a time point at the end of the time period. In some examples, the monitoring system 108 may perform the following Equation 1:

$$\bar{x}_{Cor} = \bar{x}_{Raw} + \frac{mT}{2} \qquad \text{Equation 1}$$

wherein $\bar{x}_{Cor}$ is the corrected average, $\bar{x}_{Raw}$ is the average of all of the measurements determined during the time period, m is the slope of the line-of-best-fit, and T is the time period over which the measurements are determined. The corrected average may be defined as the estimated measurement at the end of the time period. Accordingly, certain implementations of the average can account for trends in the measurements over the course of the time period.

In particular implementations, the monitoring system 108 may determine a circadian offset. In some cases, the monitoring system 108 may determine the circadian offset of an individual based on a first set of measurements determined in a first time period and a second set of measurements determined in a second time period, wherein the first time period and the second time period are at least partially 24 hours apart. For instance, the center of the first time period and the center of the second time period can be 24 hours apart. In certain examples, the second time period may be at least, in part, 24 hours before the first time period. In some cases, a length of the first time period may be different than a length of the second time period. According to particular implementations, the earlier of the first and second time periods can be longer than the later of the first and second time periods. In some examples, the earlier time period may be 1-10 times as long as the later time period. In particular implementations, the circadian offset may be determined by subtracting an average measurement of the earlier time period by an average measurement of the later time period.

In some examples, the circadian offset may be determined by subtracting a corrected average corresponding to an earlier time point from a corrected average corresponding to a later time point, wherein the earlier time point may be 24 hours prior to the later time point.

According to various implementations, the monitoring system 108 may further compare at least one metric associated with an individual to at least one normal range corresponding to the metric. In some cases, the monitoring system 108 can determine whether an average measurement of a biological condition of the individual may be outside of a normal range. The normal range may be a predetermined range of the biological condition for healthy individuals. In some cases, a normal range may be customized for a particular individual. For instance, an individual who may be known to have a relatively low resting heart rate may have a customized normal range for heart rate that has a lower minimum threshold than a standardized normal range for heart rates of the population at large. If the biological condition may be outside of the normal range, the monitoring system 108 may determine that the individual may be likely to require further assistance (e.g., critical care assistance) and/or treatment from care providers. For example, a normal range for a systolic blood pressure may be between 90 and 120 mmHg, a normal range for a diastolic blood pressure may be between 60 and 80 mmHg, a normal range for a heart rate may be 60 to 100 beats per minute, a normal range for a temperature may be between 97 and 99° F., a normal range for a respiration rate may be between 12 and 20 breaths per minute, a normal range for a blood oxygen saturation may be 95 to 100 mmHg, and so on.

In particular implementations, the monitoring system 108 can determine a warning score associated with the individual. The warning score may be determined based on one or more measurements determined from the individual. In some cases, the warning score can be an aggregated value based on multiple measurements. In particular implementations, the warning score can be weighted, such that larger deviations of measurements can provide greater earning score values. Examples of warning scores determined by the monitoring system 108 can include a Pediatric Early Warning Score (PEWS) a Modified Early Obstetric Warning Score (MEOWS) a Modified Early Warning Score (MEWS), an Early Warning Score (EWS), a National Early Warning Score (NEWS1 and NEWS2), and the like. A warning score can indicate, to a healthcare provider, whether an individual may be likely to require critical care intervention and/or transfer to an ICU.

NEWS2, for example, can be used to estimate whether a patient requires critical care intervention. NEWS2 provides a single numerical value based on a patient's vital signs, wherein the vital signs include respiration rate, $SpO_2$) (defined according to a Scale 1 or a Scale 2, as defined according to National Health Service (NETS) guidelines), exposure to air or supplemental oxygen, systolic blood pressure, pulse, level of consciousness, and temperature. The monitoring system 108 can determine an additive factor for each vital sign, based on which of multiple ranges each vital sign fits into. The single numerical value can be determined by summing the additive factors together. The following Table 1 provides example additive factors corresponding to each vital sign:

TABLE 1

| Additive Factor | 3 | 2 | 1 | 0 | 1 | 2 | 3 |
|---|---|---|---|---|---|---|---|
| Respiration Rate (per minute) | ≤8 | | 9-11 | 12-20 | | 21-24 | ≥25 |
| $SpO_2$ Scale 1 (%) | ≤91 | 92-93 | 94-95 | ≥96 | | | |
| $SpO_2$ Scale 2 (%) | ≤83 | 84-85 | 86-87 | 88-92 ≥93 (Air) | 93-94 (O2) | 95-96 (O2) | ≥97 (O2) |
| Air or $O_2$ | | | $O_2$ | Air | | | |
| Systolic Blood Pressure (mmHg) | ≤90 | 91-100 | 101-110 | 111-219 | | | ≥220 |
| Pulse (per minute) | ≤40 | | 41-50 | 51-90 | | | ≥131 |
| Consciousness | | | | Alert | | | CVPU |
| Temperature (° C.) | ≤35 | | 35.1-36 | 36.1-38 | 38.1-39 | ≥39.1 | | wherein "CVPU" stands for "Confusion but responds to Voice and Pain or Unresponsive." Accordingly, a hypercapnic patient (for which $SpO_2$ Scale 2 is utilized) with a respiration rate of 15 breaths per minute, an $SpO_2$ of 90%, a systolic blood pressure of 200 mmHg, a pulse of 60 beats per minute, a temperature of 37° C., and who has not been provided supplemental oxygen and who is alert, may have a NEWS2 score of 0. In another example, a non-hypercapnic patient (for which $SpO_2$ Scale 2 is utilized) with a respiration rate of 15 breaths per minute, an $SpO_2$ of 97%, a systolic blood pressure of 200 mmHg, a pulse of 60 beats per minute, a temperature of 37° C., and who has not been provided supplemental oxygen and who is alert, may have a NEWS2 score of 0. Notably, the NEWS2 score can range from 0 to 24. According to various implementations, the sensor devices 104-1 to 104-$n$ may automatically measure any of the vital signs considered in the NEWS2 score, and the monitoring system 108 can determine the NEWS2 score based on the measurements determined by the sensor devices 104-1 to 104-$n$.

In certain examples, the monitoring system 108 can compare the warning score of the individual to a threshold. In particular implementations, the threshold for the warning score may be predetermined. In the case of NEWS2, the threshold may be a threshold of 5, which may be known to be statistically linked to increased likelihood of death or admission to an ICU. If the warning score may be greater than the threshold, the monitoring system 108 may determine that the individual may be likely to require further assistance and/or treatment from care providers.

According to particular implementations, the monitoring system 108 can determine a circadian offset of an individual. Various biological conditions of an individual vary cyclically with the individual's sleep schedule. In many cases, an individual's periodic sleep schedule has period of 24 hours. The monitoring system 108, in particular implementations, may determine an individual's circadian offset based on the measurements determined by the sensor devices 104-1 to 104-$n$. The circadian offset may be defined according to the following Equation 2:

$$c = m_t - m_{t-24} \qquad \text{Equation 2}$$

wherein c is the circadian offset, m is a metric, $m_t$ is the metric at time t, and $m_{t-24}$ is the metric at 24 hours prior to t. The metric m may be a vital sign or a warning score, in various examples. In some cases, t can represent a current time.

In some cases, the metric can be an average metric. According to particular examples, the metric $m_t$ may be an average metric (e.g., a corrected average metric) over a first time period and the metric $m_{t-24}$ may be an average metric (e.g., a corrected average metric) over a second time period. The first time period may be at least partially 24 hours after the second time period. In some cases, the second time period can be longer than the first time period. Accordingly, unusual variations in the metric during the previous day are less likely to trigger high circadian offsets in the next day.

In particular implementations, the monitoring system 108 may determine whether the circadian offset may be outside of a normal range. In particular implementations, a normal range for an individual's circadian offset of a particular health indicator can be about half of the individual's normal variation of the particular health indicator over the course of a 24-hour period. For example, if an individual's respiratory rate ranges from 12 cycles per minute to 16 cycles per minute, the normal range for the individual's circadian offset of the respiratory rate can be $(16-12)/2=\pm2$. In various examples, the normal range of a circadian offset can be referred to as a "stable range."

When the circadian offset is outside of the normal range, the monitored individual may be deteriorating and require additional medical care. In certain cases, an absolute value of the circadian offset may be determined and compared to a threshold. When the absolute value of the circadian offset is above the threshold, the monitored individual may be deteriorating and require additional medical care. In some cases, the normal range can be a predetermined range of circadian offsets indicating that an individual may be unlikely to require critical care.

The monitoring system 108 may be in further communication with an Electronic Medical Record (EMR) system 110 over a second network 112. The EMR system 110 may store various health record information and selectively transmit data indicating the health record information to the monitoring system 108. The monitoring system 108 may further analyze the measurements made by the sensor devices 104-1 to 104-n in view of the health record information. For instance, the health record information may indicate that an individual is receiving supplemental $O_2$, and the monitoring system 108 may determine the NEWS2 for the individual based on whether the individual is receiving supplemental $O_2$.

The monitoring system 108 may be in communication with first to mth clinical devices 114-1 to 114-m over a third network 116, wherein m is a positive integer. In various implementations, the monitoring system 108 may selectively report information about the individuals 102-1 to 102-n to the clinical devices 114-1 to 114-m. The information may be indicated in data transmitted from the monitoring system 108 to the clinical devices 114-1 to 114-m. In some cases, the monitoring system 108 may control, or otherwise cause at least one user interface associated with the clinical devices 114-1 to 114-m, In various implementations, the monitoring system 108 may cause at least one of the clinical devices 114-1 to 114-m to output an alert associated with an individual based on at least one health indicator of the individual. As used herein, the term "health indicator" may refer to at least one of a vital sign, a warning score, or a circadian offset. The monitoring system 108 may cause at least one of the clinical devices 114-1 to 114-m to output the alert by transmitting, to the clinical device, data instructing the clinical device to output the alert. The data may identify the individual by at least one of name, bed number, location, identification number, demographics, or the like. In some cases, the data may further indicate which health indicator indicates the individual requires further care.

According to some examples, the monitoring system 108 may cause at least one of the clinical devices 114-1 to 114-m to output the alert in response to determining that at least one health indicator of the individual may be variant (e.g., at least one health indicator is outside of a normal range, is below a threshold, is above a threshold, or the like). In some cases, the monitoring system 108 may only output the alert in response to determining that multiple health indicators are variant. For instance, the monitoring system 108 may instruct the first clinical device 114-1 to output an alert associated with the first individual 102-1, when both a vital sign and a circadian offset of the first individual 102-1 are determined to be outside of normal ranges for the first individual 102-1, but may refrain from instructing the first clinical device 114-1 to output the alert when the vital sign is outside of a normal range for the first individual 102-1 but the circadian offset is within a normal range for the first individual 102-1.

The clinical devices 114-1 to 114-m may output alerts in various manners. In some cases, the clinical devices 114-1 to 114-m may output the alert as auditory signals that can be heard by at least one care provider. For example, the clinical devices 114-1 to 114-m could be pagers that output an alarm indicating that a care provider should call another care provider or should attend an individual directly. In particular implementations, the clinical devices 114-1 to 114-m may output the alert as a haptic signal that can be felt by at least one care provider. For instance, the clinical devices 114-1 to 114-m may vibrate. According to various implementations, the clinical devices may output the alert as visual signals. In some examples, the clinical devices 114-1 to 114-m may display pop-ups, blinking icons, colors, and various user interface elements portraying the alert. The alerts may be provided on various user interfaces of the clinical devices 114-1 to 114-m.

The alerts output by the clinical devices 114-1 to 114-m may prompt care providers to monitor the individuals 102-1 to 102-n associated with the alerts. In some cases, the alerts can be disabled by at least one care provider via the user interfaces. For instance, an alert indicating that the first individual 102-1 requires additional attention can be disabled in response to a care provider acknowledging the alert and/or reaching the first individual's 102-1 bedside.

Figure 2:
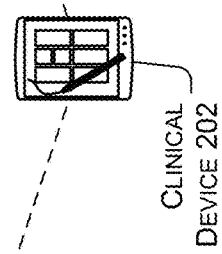
FIG. 2 illustrates an example user interface displayed by a clinical device.

FIG. 2 illustrates an example user interface 200 displayed by a clinical device 202. In some examples, the clinical device 202 may correspond to any of the clinical devices 114-1 to 114-m described above with reference to FIG. 1.

According to various implementations, the clinical device 202 may be utilized by at least one care provider responsible for monitoring multiple patients. The clinical device 202 may display a table that indicates whether any of the multiple patients are in need of additional care. The table includes a column identifying the patients (e.g., first through nth individuals), warning scores associated with the patients, circadian offsets of the patients, and statuses of the patients.

As shown in FIG. 2, the first individual has a "normal" status. The status of the first individual may indicate that the warnings score of the first individual may be below a threshold (e.g., 2 is below the threshold). The status of the individual may indicate that the circadian offset of the first individual may be within a normal range (e.g., 1 is within a normal range).

On the other hand, the nth individual has an "ALERT" status. The status of the nth individual may indicate that the warnings score of the nth individual may be above a threshold (e.g., 7 is above the threshold). The status of the individual may indicate that the circadian offset of the first individual may be outside of a normal range (e.g., 5 is outside of a normal range).

The user interface 200 may emphasize the ALERT status of the nth individual in a variety of ways. For example, a row of the table associated with the nth individual may be a color (e.g., red) that may be different than a color (e.g., green) of the row(s) of the table associated with individuals that do not have the ALERT status. In some instances, text in the row of the table associated with the nth individual may be selectively bolded. According to some examples, the row of the table associated with the nth individual may blink.

Figure 3A:
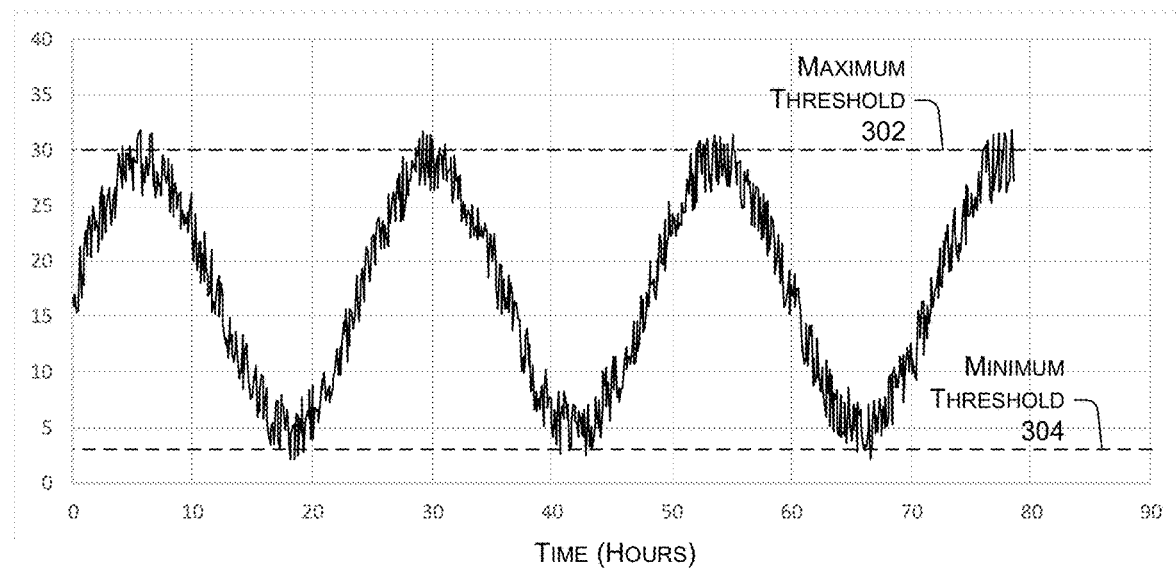
FIGS. 3A to 3D illustrate examples of health indicators determined for an individual that does not require additional care.

FIGS. 3A to 3D illustrate examples of health indicators determined for an individual that does not require additional care. FIG. 3A illustrates a graph of a semi-continuous dataset associated with a vital sign measured over the course of multiple days. An x axis of the graph represents time in hours. A y axis of the graph represents the measured vital sign. A maximum threshold 302 and a minimum threshold 304 may represent a normal range for the illustrated vital sign.

As illustrated in FIG. 3A, the example vital sign varies randomly due to random noise. In addition, the vital sign varies periodically over the course of each 24-hour cycle based on circadian offsets. Both the noise and the circadian offsets cause the dataset to exceed the maximum threshold 302 and fall below the minimum threshold 304 at various points throughout each day. Accordingly, if care providers were alerted whenever the dataset is outside of the range represented by the maximum threshold 302 and the minimum threshold 304, the care providers may be unnecessarily alerted multiple times, even though the monitored individual does not require additional care.

Figure 3B:
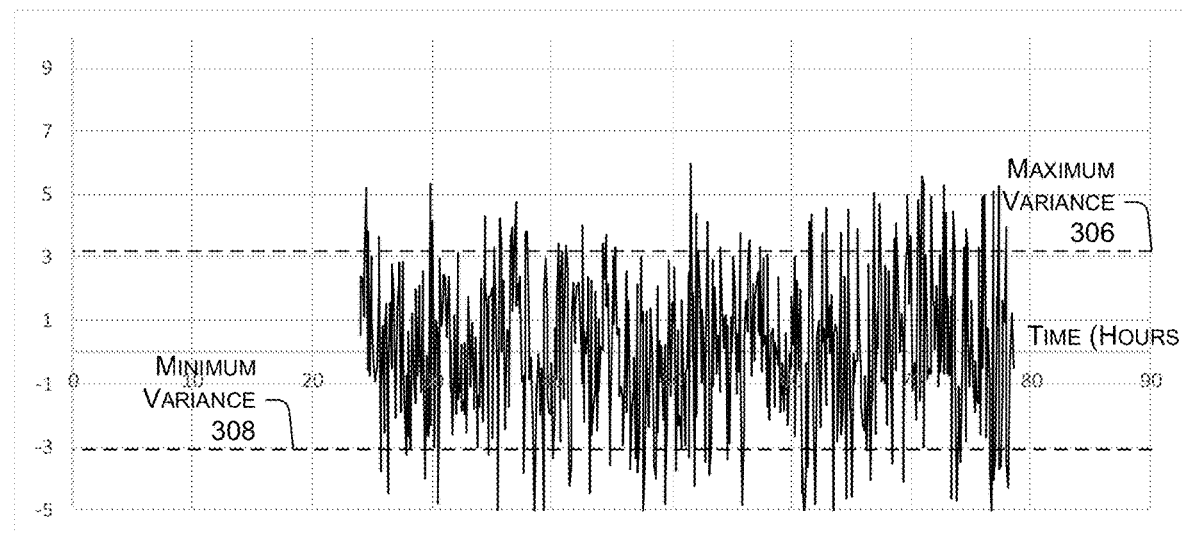

FIG. 3B illustrates a graph of a circadian offset of the vital sign illustrated in FIG. 3A. An x axis of the graph represents time in hours. A y axis of the graph represents the circadian offset of the vital sign. A maximum variance 306 and a minimum variance 308 may represent a normal range for the circadian offset.

As illustrated, the example circadian offset omits the periodic, 24-hour cycle variations in the vital sign. However, due to the noise associated with the vital sign, the circadian offset illustrated in FIG. 3B still varies outside of the maximum variance 306 and the minimum variance 308.

Figure 3C:
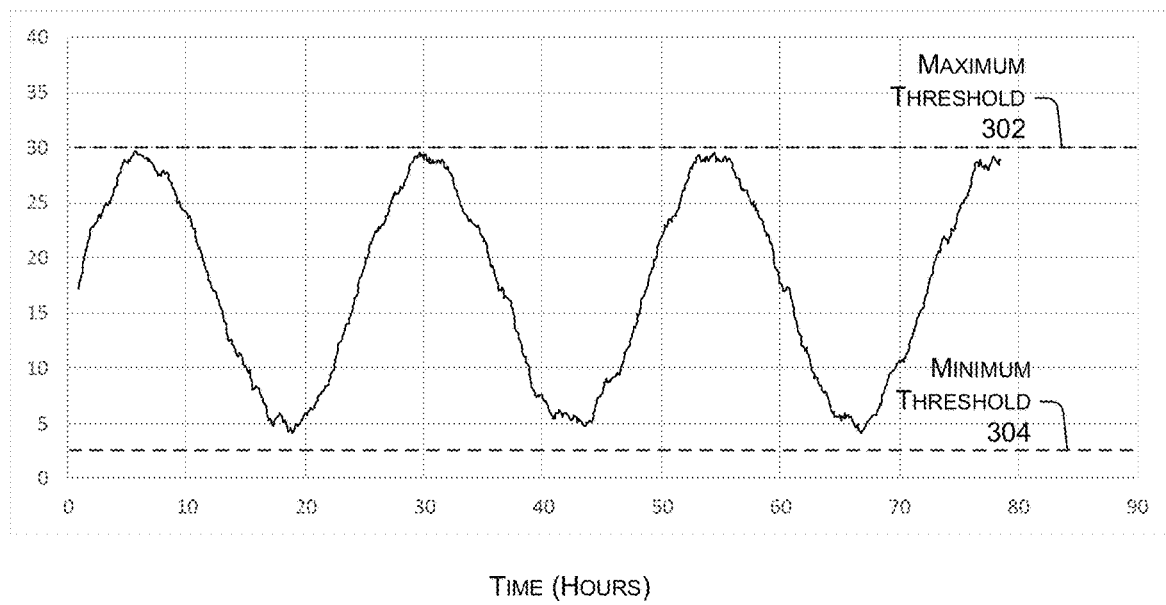

FIG. 3C illustrates a graph of a running average of the semi-continuous vital sign dataset of FIG. 3A. An x axis of the graph represents time in hours. A y axis of the graph represents the running average of the measured vital sign. In the particular example illustrated in FIG. 3C, the vital sign is averaged over the course of an hour.

As illustrated in FIG. 3C, the running average significantly reduces the impact of the random noise in the dataset of FIG. 3A. Using the same maximum threshold 302 and the same minimum threshold 304, the running average effectively eliminates the chance that the care provider will be alerted when the individual does not require additional care.

Figure 3D:
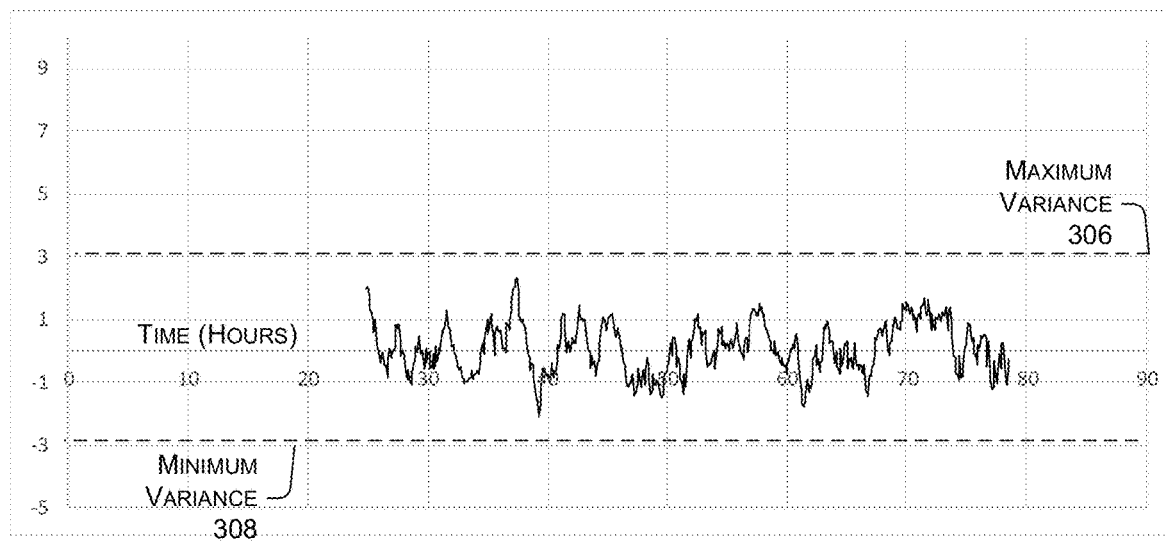

FIG. 3D illustrates a graph of a circadian offset of the running average illustrated in FIG. 3D. An x axis of the graph represents time in hours. A y axis of the graph represents the circadian offset of the average vital sign. In the particular example illustrated in FIG. 3D, the circadian offset represents the difference between an hourly vital sign at a particular time period and the hourly vital sign 24 hours prior to the particular time period.

Unlike the circadian offset depicted in FIG. 3B, the circadian offset depicted in FIG. 3D varies within the normal range represented by the maximum variance 306 and the minimum variance 308. Accordingly, the circadian offset of the running average effectively eliminates the chance that the care provider would be alerted when the individual does not require additional care.

Figure 4A:
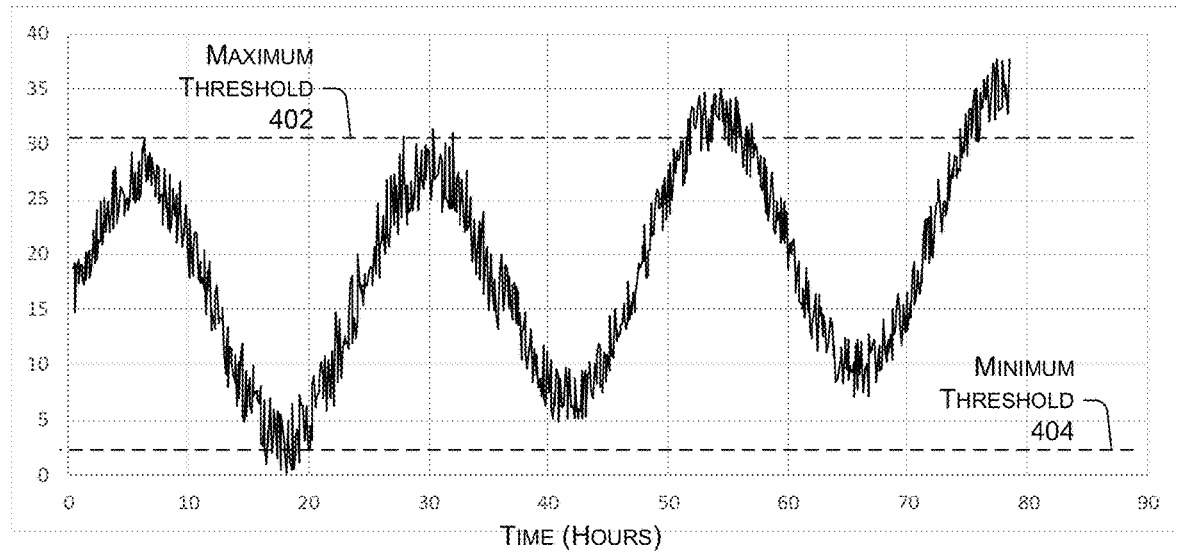
FIGS. 4A to 4D illustrate examples of health indicators determined for an individual that may require additional care.

FIGS. 4A to 4D illustrate examples of health indicators determined for an individual that may require additional care. FIG. 4A illustrates a graph of a semi-continuous dataset associated with a vital sign measured over the course of multiple days. An x axis of the graph represents time in hours. A y axis of the graph represents the measured vital sign. A maximum threshold 402 and a minimum threshold 404 may represent a normal range for the vital sign.

As illustrated in FIG. 4A, the vital sign varies randomly due to random noise. In addition, the vital sign varies periodically over the course of each 24-hour cycle based on circadian offsets. Both the noise and the circadian offsets cause the dataset to exceed the maximum threshold 402 at various points throughout each day. However, due to the noise and circadian offsets, the vital sign may linger between the maximum threshold 402 and the minimum threshold 404 even though the individual may require additional care. For instance, the vital sign of FIG. 4A would not notify a care provider that the individual's health may be deteriorating between 60 hours and 70 hours.

Figure 4B:
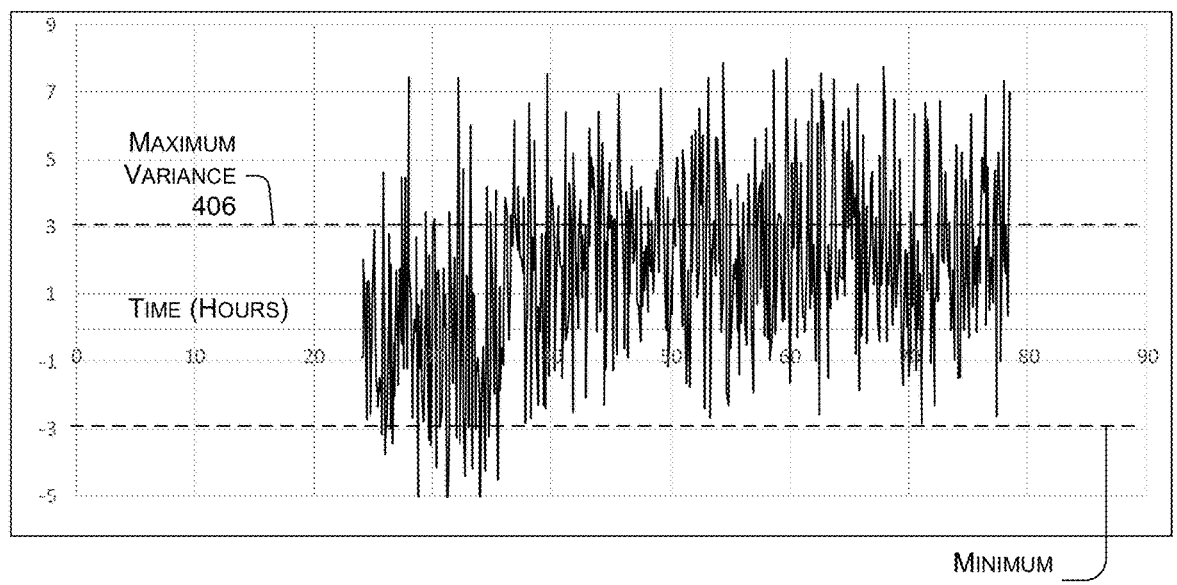

FIG. 4B illustrates a graph of a circadian offset of the vital sign illustrated in FIG. 4A. An x axis of the graph represents time in hours. A y axis of the graph represents the circadian offset of the vital sign. A maximum variance 406 and a minimum variance 408 may represent a normal range for the circadian offset.

As illustrated, the circadian offset omits the periodic, 24-hour cycle variations in the vital sign. The circadian offset illustrated in FIG. 4B varies outside of the maximum variance 406 and the minimum variance 408 as early as about 26 hours, even though the individual may not be deteriorating until after the 40 hour mark.

Figure 4C:
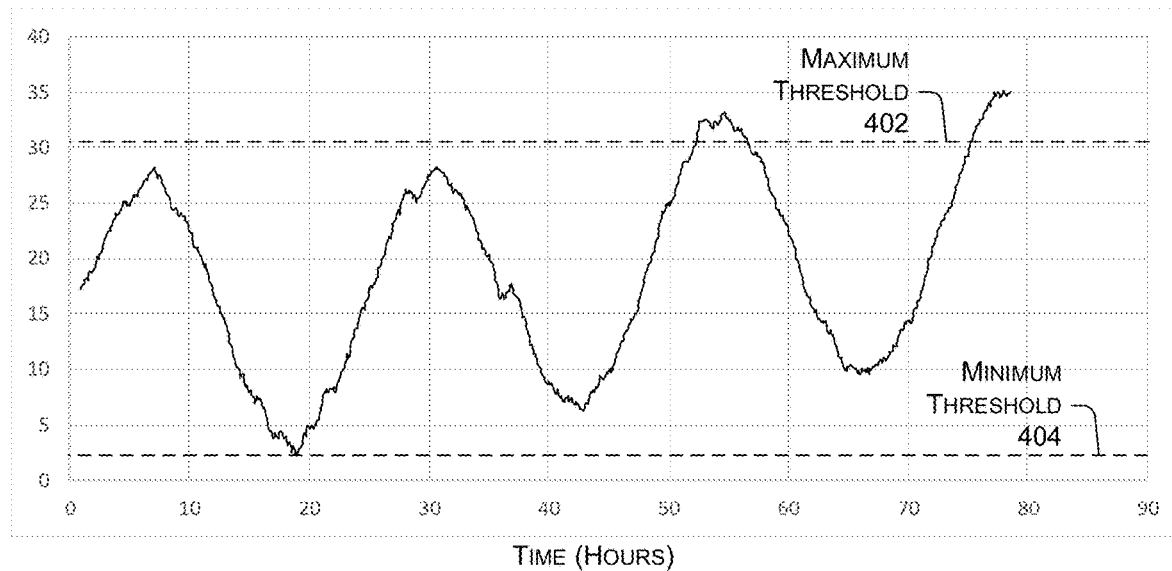

FIG. 4C illustrates a graph of a running average of the semi-continuous vital sign dataset of FIG. 4A. An x axis of the graph represents time in hours. A y axis of the graph represents the running average of the measured vital sign. In the particular example illustrated in FIG. 4C, the vital sign is averaged over the course of an hour.

As illustrated in FIG. 4C, the running average significantly reduces the impact of the random noise in the dataset of FIG. 4A. Using the same maximum threshold 402 and the same minimum threshold 404, the running average effectively ensures that a care provider can be selectively notified as the individual's condition deteriorates.

Figure 4D:
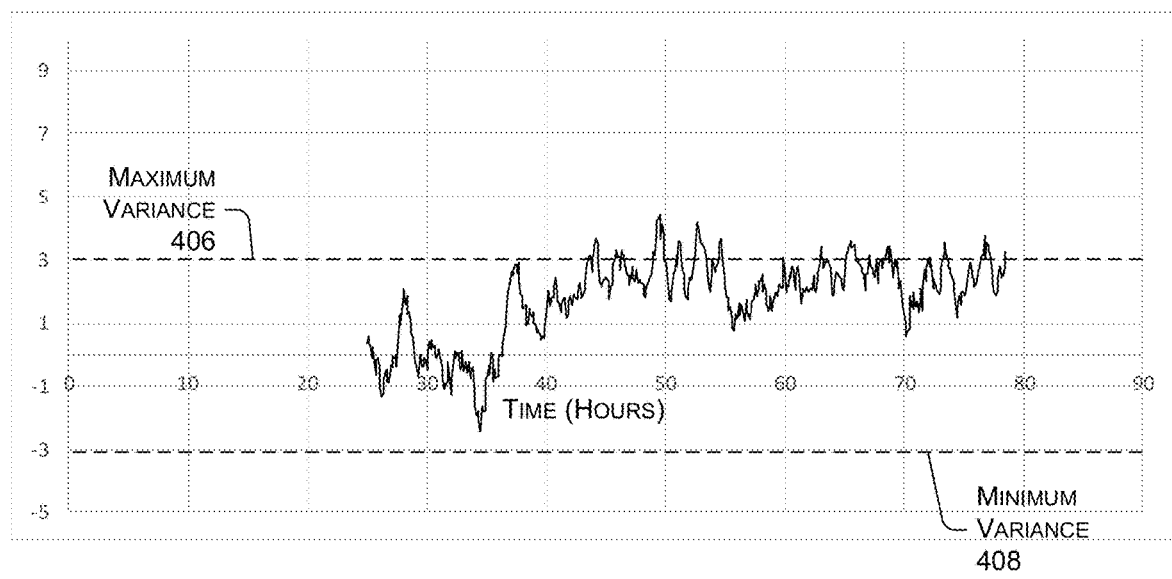

FIG. 4D illustrates a graph of a circadian offset of the running average illustrated in FIG. 4D. An x axis of the graph represents time in hours. A y axis of the graph represents the circadian offset of the average vital sign. In the particular example illustrated in FIG. 4D, the circadian offset represents the difference between an hourly vital sign at a particular time period and the hourly vital sign 24 hours prior to the particular time period.

Unlike the circadian offset depicted in FIG. 4B, the circadian offset depicted in FIG. 4D only exceeds the maximum variance 406 after about 44 hours. Accordingly, a care provider can be assured that any alerts triggered due to the circadian offset of FIG. 4D are more likely to be accurate than alerts triggered due to the circadian offset of FIG. 4B. In particular, the circadian offset of FIG. 4D indicates that the individual's condition has deteriorated between the hours of 60 and 70.

Figure 5:
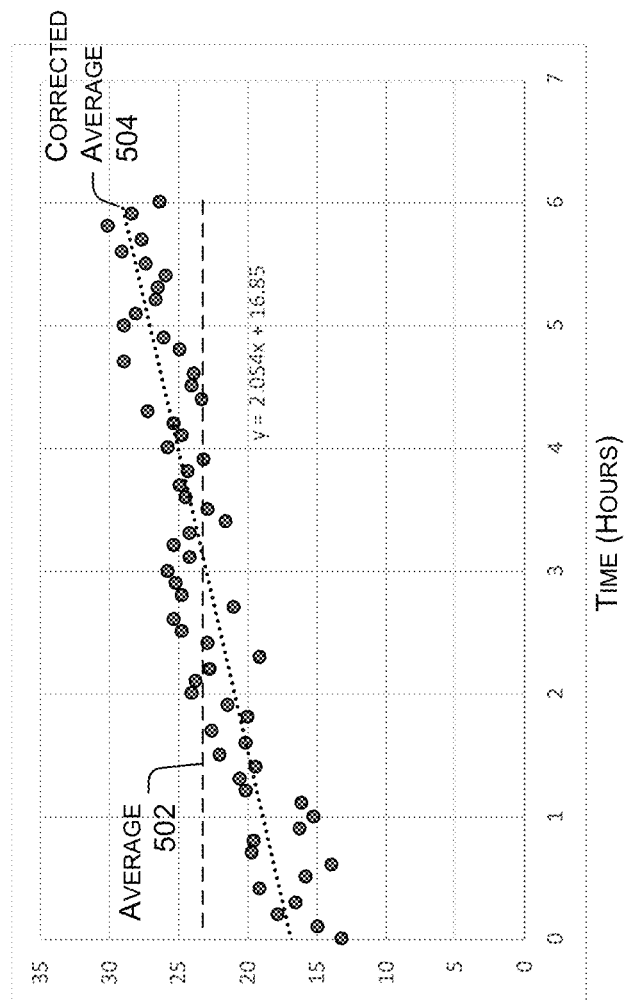
FIG. 5 illustrates a graph providing an example of correcting an average based on a trend.

FIG. 5 illustrates a graph providing an example of correcting an average 502 based on a trend. An x axis of the graph represents time in hours. A y axis of the graph represents vital signs of an individual that are measured during a particular time period.

In various implementations, the particular time period depicted in FIG. 5 may be significantly less than 24 hours. Accordingly, even if the measurements vary periodically over the course of 24 hours, the circadian offset may be relatively negligible over the course of the particular time period. As illustrated in FIG. 5, the time period is 6 hours, but in certain implementations, the time period could be between 0.5-8 hours.

A linear line-of-best fit may be determined for the measurements over the course of the time period. According to various implementations, linear interpolation can be performed on the measurements. The line-of-best-fit may be represented by the following Equation 3:

$$y=mx+b \qquad \text{Equation 3}$$

wherein y represents the measurements, m is the slope of the line, x represents time, and b represents the y-intercept of the line-of-best-fit.

An average 502 of the measurements may be determined based on the measurements. The average 502 may be considered to be a raw average and may be determined by summing all of the measurements and dividing the sum by the time period. A corrected average 504 may be determined based on the slope m of the line, the time period over which the measurements were acquired, and the average 502 of the measurements. The corrected average 504 may be determined based on Equation 1, described above with reference to FIG. 1.

In various implementations, the corrected average 504 may be determined to represent the vital sign at time=6 hours, rather than the raw average 502. Accordingly, the trend over the course of the time period may be considered.

Figure 6:
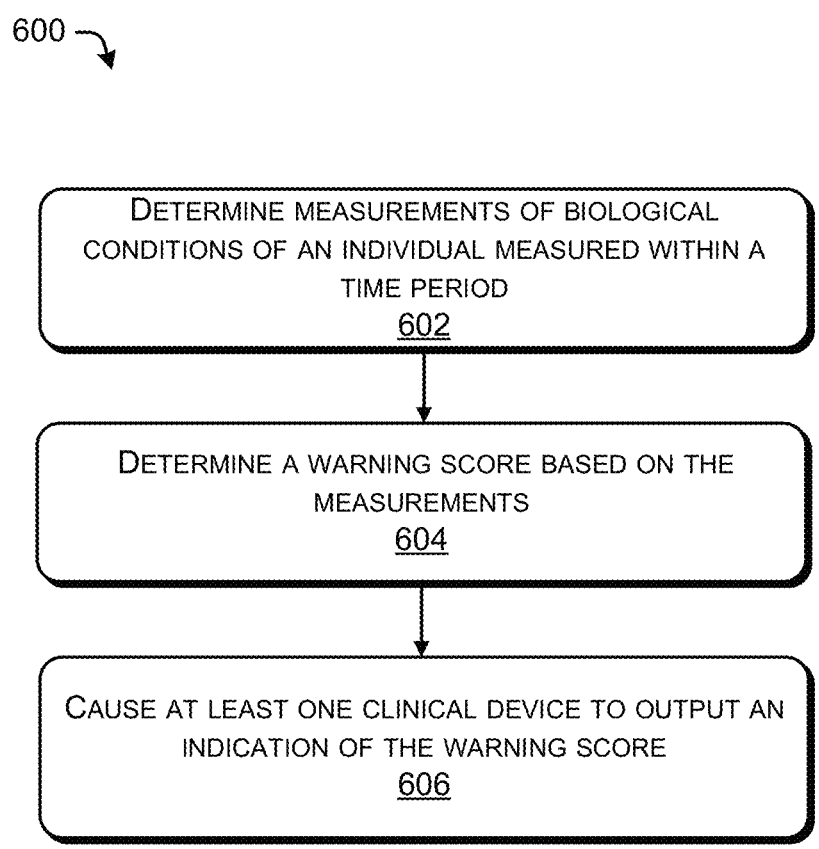
FIG. 6 illustrates a process for determining and reporting a warning score of an individual.

FIG. 6 illustrates a process 600 for determining and reporting a warning score of an individual. In various implementations, process 600 can be performed by at least one of a sensor device (e.g., sensor devices 104-1 to 104-n), a monitoring system (e.g., the monitoring system 108), or a clinical device (e.g., clinical devices 114-1 to 114-m). In certain cases, the process 700 can be performed by a system including at least one processor.

At 602, the processor(s) can determine measurements of biological conditions of an individual that were measured within a time period. In some cases, at least one sensor (e.g., sensor devices 104-1 to 104-n) can determine various parameters associated with the biological conditions, generate signals based on the parameters, and transmit the signals to the processor(s). The measurements may be semi-continuous. In some cases, the sensor(s) may determine the parameters automatically and without warning to the individual. Accordingly, in some cases, the measurements may be susceptible to random noise. For instance, the sensor(s) may include an electronic blood pressure monitor that automatically tightens around the individual's arm, measures various parameters (e.g., an electrical signal) that are indicative of the individual's blood pressure during the time period, and transmits signals indicative of the individual's blood pressure to the processor(s).

In particular implementations, the signals can be transmitted between the processor(s) and the sensor(s) via a transceiver in communication with the processor(s) and a transceiver in communication with the sensor(s). For example, the processor(s) may receive the signals indicative of the measurements from the sensor(s). In some cases, the transceiver in communication with the sensor(s) may wirelessly transmit the signals indicative of the measurements to the transceiver in communication with the processor(s) The transceiver in communication with the processor(s) may wirelessly receive the signals from the transceiver in communication with the sensor(s).

The biological conditions may include vital signs, in some cases. For instance, the measurements of the biological conditions may include at least one of a respiratory rate of the individual, a body temperature of the individual, a blood pressure of the individual, a heart rate of the individual, whether the individual may be using supplemental oxygen, a consciousness of the individual, or the like.

According to some implementations, the time period may be shorter than a 24-hour time period. The time period may be significantly (e.g., at least ten times) as long as a sampling period of the measurements. In some cases, the time period can be between one half an hour and eight hours.

At 604, the processor(s) may determine a warning score based on the measurements. The warning score may represent any single metric that aggregates multiple biological conditions, such as the biological conditions indicated in the measurements that were received at 602. The National Early Warning Score (NEWS2) is one example of a warning score determined by the processor(s) at 604.

In particular implementations, the processor(s) may determine the warning score based on a running average of each of the biological conditions over the course of the time period. In some cases, the running average of a particular biological condition may be corrected based on a line-of-best-fit. The line-of-best-fit may be determined by the processor(s) for the measurements of the particular biological condition over the course of the time period. Accordingly, processor(s) may prevent the random noise in the measurements from propagating to the warning score.

At 606, the processor(s) may cause at least one clinical device to output an indication of the warning score. The processor(s) may be in communication with the clinical device(s) via one or more wired or wireless interfaces, in certain examples. According to some implementations, the processor(s) may cause a transceiver in communication with the processor(s) to transmit signals indicative of the warning score to at least one transceiver in communication with the clinical device(s). The processor(s) may cause the clinical device(s) to output the indication of the warning score by causing the transceiver to transmit the signals to the clinical device(s). In certain examples, the processor(s) may transmit (e.g., cause transmission via a transceiver) a signal indicating an instruction to output the indication of the warning score to the clinical device(s).

In various implementations, the clinical device(s) may output the indication via a user interface. The clinical device(s) may output the indication as at least one of an auditory signal, a haptic signal, or a visual signal. For example, the clinical device(s) may display, on a screen, a visual representation of the warning score.

In particular implementations, the processor(s) may determine that the warning score may be outside of a predetermined range. For instance, if the warning score is a NEWS2 score, the processor(s) may determine that the warning score is at least 3. In response to determining that the warning score is outside of the predetermined range, the processor(s) may cause the clinical device(s) to output the indication as an alert associated with the individual. The alert may indicate to any care provider interacting with the clinical device(s) that the individual may be likely to require critical care. For instance, a speaker associated with the clinical device(s) may output an alarm in response to the processor(s) transmitting a signal indicating an alert to the clinical device(s).

In some cases, the clinical device(s) may output indications of warning scores and other health indicators of multiple patients, including the individual. When one of the warning scores is outside of a predetermined range (e.g., the warning score is greater than a threshold), the clinical device(s) may selectively activate an alert for an individual corresponding to the warning score. In some cases, the warning scores of other individuals may remain output by the clinical device(s). Accordingly, care providers can continuously monitor the warning scores of multiple patients using a single user interface and can be immediately notified when any of those patients are likely to require critical care.

Figure 7:
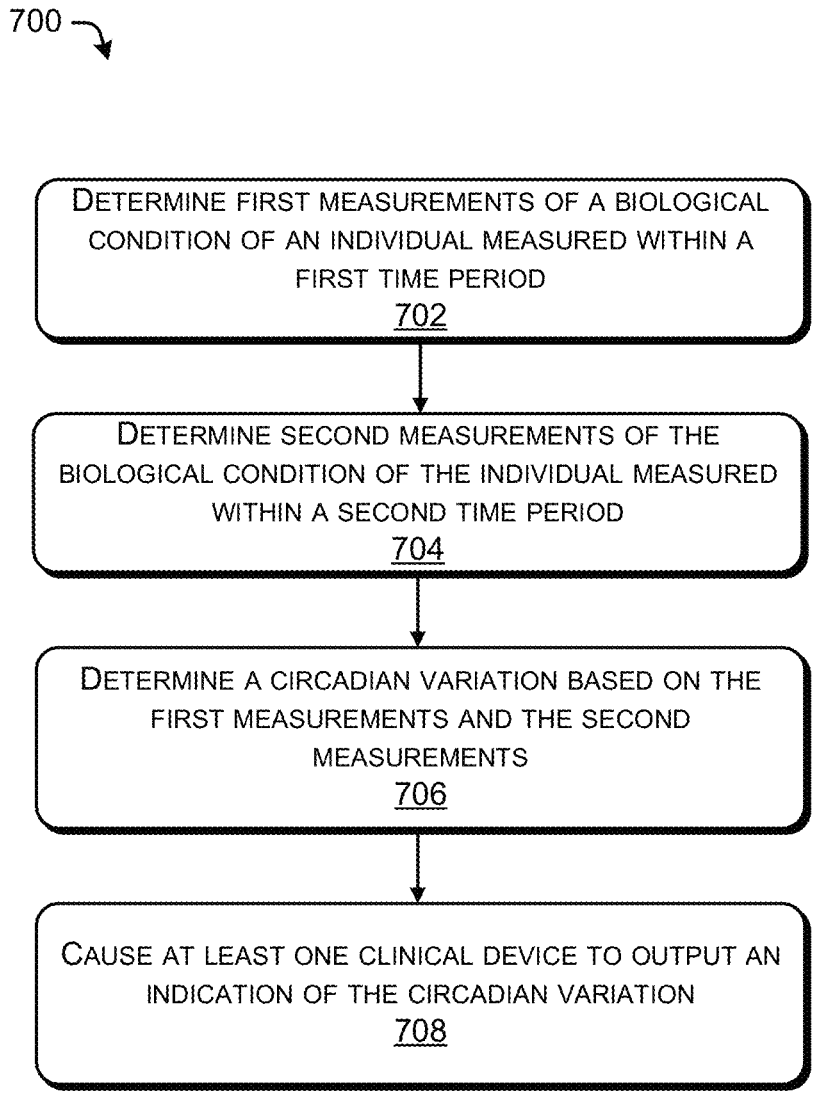
FIG. 7 illustrates an example process for determining and reporting a circadian offset of an individual.

FIG. 7 illustrates an example process 700 for determining and reporting a circadian offset of an individual. In various implementations, process 700 can be performed by at least one of a sensor device (e.g., sensor devices 104-1 to 104-*n*), a monitoring system (e.g., the monitoring system 108), or a clinical device (e.g., clinical devices 114-1 to 114-*m*). In certain cases, the process 700 can be performed by a system including at least one processor.

At 702, the processor(s) may determine first measurements of a biological condition of an individual that were measured determined within a first time period. In some cases, at least one sensor (e.g., sensor devices 104-1 to 104-*n*) may measure various parameters associated with the individual, determine signals indicating the first measurements using the measured parameters, and transmit the signals to the processor(s). The first measurements may be semi-continuous. In some cases, the sensor(s) may measure the various parameters automatically and without warning to the individual. Accordingly, in some cases, the first measurements may be susceptible to random noise. For instance, the sensor(s) may include an electronic blood pressure monitor that automatically tightens around the individual's arm, measures various parameters (e.g., an electrical signal) that are indicative of the individual's blood pressure during the time period, and transmits signals indicative of the individual's blood pressure to the processor(s).

In particular implementations, the signals can be transmitted between the processor(s) and the sensor(s) via a transceiver in communication with the processor(s) and a transceiver in communication with the sensor(s). For example, the processor(s) may receive the signals indicative of the first measurements from the sensor(s). In some cases, the transceiver in communication with the sensor(s) may wirelessly transmit the signals indicative of the first measurements to the transceiver in communication with the processor(s). The transceiver in communication with the processor(s) may wirelessly receive the signals from the transceiver in communication with the sensor(s).

The biological conditions may include a vital sign, in some cases. For instance, the first measurements of the biological conditions may include at least one of a respiratory rate of the individual, a body temperature of the individual, a blood pressure of the individual, a heart rate of the individual, whether the individual may be using supplemental oxygen, a consciousness of the individual, or the like.

According to some implementations, the first time period may be shorter than a 24-hour time period. The first time period may be significantly (e.g., at least ten times) as long as a sampling period of the measurements. In some cases, the first time period can be between one half an hour and eight hours.

At 704, the processor(s) may determine second measurements of the biological condition of the individual that were measured within a second time period. In some cases, at least one sensor (e.g., sensor devices 104-1 to 104-*n*) may measure various parameters associated with the individual, determine signals indicating the second measurements using the measured parameters, and transmit the signals to the processor(s). The second measurements may be semi-continuous. In some cases, the sensor(s) may measure the parameters automatically and without warning to the individual. For instance, the sensor(s) may include an electronic blood pressure monitor that automatically tightens around the individual's arm, measures various parameters (e.g., an electrical signal) that are indicative of the individual's blood pressure during the second time period, and transmits signals indicative of the individual's blood pressure to the processor(s).

In particular implementations, the signals can be transmitted between the processor(s) and the sensor(s) via a transceiver in communication with the processor(s) and a transceiver in communication with the sensor(s). For example, the processor(s) may receive the signals indicative of the second measurements from the sensor(s). In some cases, the transceiver in communication with the sensor(s) may wirelessly transmit the signals indicative of the second measurements to the transceiver in communication with the processor(s). The transceiver in communication with the processor(s) may wirelessly receive the signals from the transceiver in communication with the sensor(s).

According to some implementations, the second time period may be shorter than a 24-hour time period. The second time period may be significantly (e.g., at least ten times) as long as a sampling period of the measurements. In some cases, the second time period can be between one half an hour and eight hours.

According to various implementations, the second time period may occur, at least in part, 24 hours after the first time period. The second time period may overlap with 24 hours after the beginning of the first time period or 24 hours after the end of the first time period. In particular implementations, a length of the second time period may be shorter than a length of the first time period. For instance, the first time period may be between one hour and eight hours, and the second time period may be between a half of an hour and 6 hours.

At 706, the processor(s) may determine a circadian offset based on the first measurements and the second measurements. In some examples, the processor(s) determine the circadian offset based on an average of the first measurements and an average of the second measurements. For instance, the circadian offset may be equal to a difference between the averages. In some cases, the processor(s) may use corrected averages of the first measurements and the second measurements to determine the circadian offset.

At 708, the processor(s) cause at least one clinical device to output an indication of the circadian offset. The processor(s) may be in communication with the clinical device(s) via one or more wired or wireless interfaces, in certain examples. According to some implementations, the processor(s) may cause a transceiver in communication with the processor(s) to transmit signals indicative of the circadian offset to at least one transceiver in communication with the clinical device(s). The processor(s) may cause the clinical device(s) to output the indication of the circadian offset by causing the transceiver to transmit the signals to the clinical device(s). In certain examples, the processor(s) may transmit (e.g., cause transmission via a transceiver) a signal indicating an instruction to output the indication of the circadian offset to the clinical device(s).

In various implementations, the clinical device(s) may output the indication via a user interface. The clinical device(s) may output the indication as at least one of an auditory signal, a haptic signal, or a visual signal. For example, the clinical device(s) may display, on a screen, a visual representation of the circadian offset.

In particular implementations, the processor(s) may determine that the circadian offset is outside of a predetermined range. In response to determining that the circadian offset is outside of the predetermined range, the processor(s) may cause the clinical device(s) to output the indication as an alert associated with the individual. The alert may indicate to any care provider interacting with the clinical device(s) that the individual may be likely to require critical care. For instance, a speaker associated with the clinical device(s) may output an alarm in response to the processor(s) transmitting a signal indicating an alert to the clinical device(s).

In some cases, the clinical device(s) may output indications of circadian offsets and other health indicators of multiple patients, including the individual. When one of the circadian offsets is outside of a predetermined range (e.g., the circadian offset is greater than a threshold), the clinical device(s) may selectively activate an alert for an individual corresponding to the circadian offset. In some cases, the circadian offsets of other individuals may remain output by the clinical device(s). Accordingly, care providers can continuously monitor the circadian offsets of multiple patients using a single user interface and can be immediately notified when any of those patients are likely to require critical care.

Figure 8:
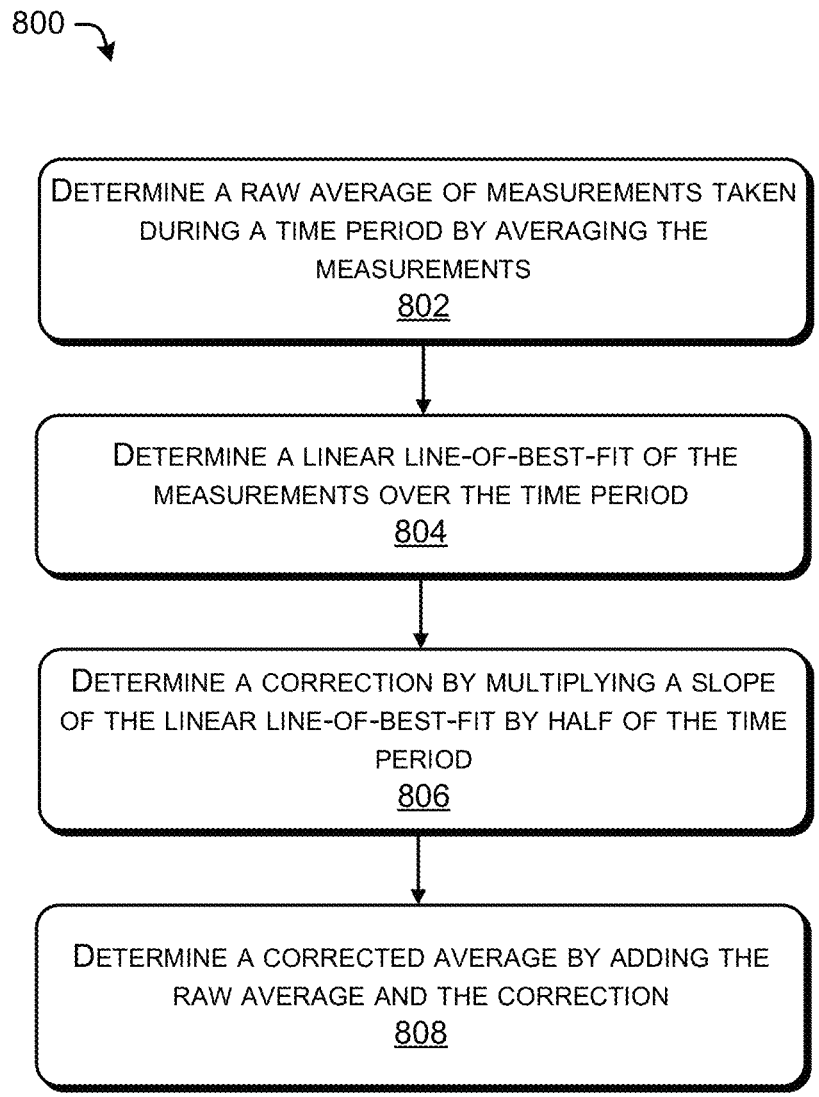
FIG. 8 illustrates a process for determining a corrected average, which may be used to determine a warning score and/or a circadian offset.

FIG. 8 illustrates a process 800 for determining a corrected average, which may be used to determine a warning score and/or a circadian offset. In various implementations, process 800 can be performed by at least one of a sensor device (e.g., sensor devices 104-1 to 104-n), a monitoring system (e.g., the monitoring system 108), or a clinical device (e.g., clinical devices 114-1 to 114-m). In some cases, the process 800 can be performed by a device including at least one processor.

At 802, the processor(s) may determine a raw average of measurements that were measured during a time period. For instance, the processor(s) may add the measurements together and divide the sum of the measurements by the time period. The measurements may represent measurements of a biological condition of an individual. The time period may be eight hours or less, in some cases, to reduce the impacts of circadian offsets.

At 804, the processor(s) may determine a linear line-of-best-fit for the measurements over the time period. For example, the processor(s) may perform linear interpolation on the measurements.

At 806, the processor(s) may determine a correction by multiplying a slope of the line-of-best-fit by half of the time period. Then, at 808, the processor(s) may determine a corrected average by adding the raw average and the correction.

In various implementations, the corrected average can be used to estimate the biological condition at the end of the time period. Unlike the raw average, the corrected average considers a trend of the biological condition throughout the time period. Accordingly, the corrected average may be a more accurate representation of the biological condition at the end of the time period than the raw average.

Figure 9:
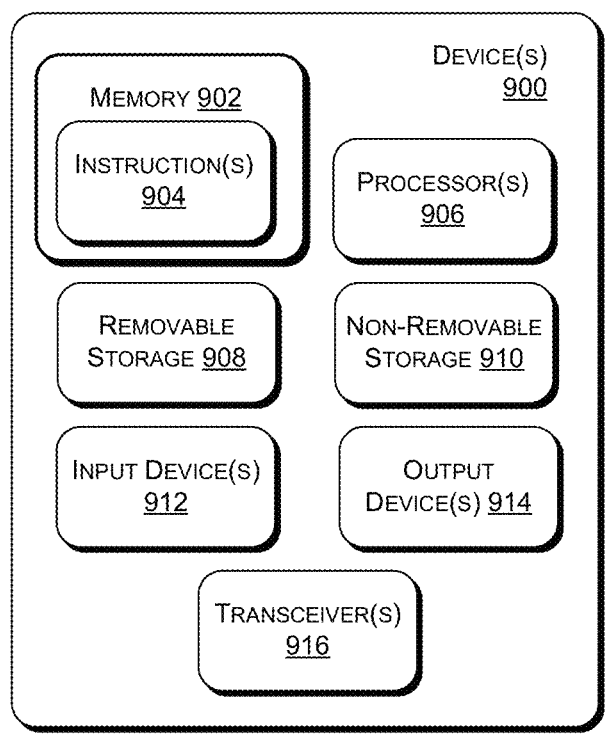
FIG. 9 illustrates an example system including at least one device.

FIG. 9 illustrates an example system including at least one device 900. In particular implementations, the system illustrated in FIG. 9 may perform any of the functionality described herein. The device(s) 900 may be implemented by at least one of server computer(s), dedicated hardware, software operating on dedicated hardware, or virtualized function(s) hosted on an appropriate platform (e.g., cloud infrastructure). The device(s) 900 may be implemented as a single device or as multiple devices with components and data distributed among them.

As illustrated, the device(s) 900 comprise a memory 902. In various implementations, the memory 902 is volatile (such as Random Access Memory (RAM)), non-volatile (such as Read Only Memory (ROM), flash memory, etc.) or some combination of the two. Various elements stored in the memory 902 can include methods, threads, processes, applications, objects, modules, or any other sort of executable instructions. Elements stored in the memory 902 may be non-transitory. The memory 902 may also store various files, databases, or the like.

The memory 902 may include various instructions 904, which can be executed by processor(s) 906 to perform operations. For instance, the instructions 904, when executed by the processor(s) 906, can cause the processor(s) 904 and/or the device(s) 900 to perform various functions of sensors (e.g., the sensors 104-1 to 104-n), a monitoring system (e.g., the monitoring system 108), an EMR system (e.g., the EMR system 110), a clinical device (e.g., the clinical devices 114-1 to 114-m), or a combination thereof. In some cases, the memory 902 sores files, databases, and/or other types of data. In some embodiments, the processor(s) 906 includes a Central Processing Unit (CPU), a Graphics Processing Unit (GPU), or both CPU and GPU, or other processing unit or component known in the art.

The device(s) 900 can also include additional data storage components such as, for example, magnetic disks, optical disks, or tape. These additional data storage components can include removable storage 908 and non-removable storage 910. Tangible computer-readable media can include volatile and nonvolatile, removable and non-removable media implemented in any method or technology for storage of information, such as computer readable instructions, data structures, program modules, or other data.

The memory 902, removable storage 908, and non-removable storage 910 are all examples of computer-readable storage media. Computer-readable storage media include, but are not limited to, RAM, ROM, EEPROM, flash memory or other memory technology, CD-ROM, Digital Versatile Discs (DVDs), Content-Addressable Memory (CAM), or other optical storage, magnetic cassettes, magnetic tape, magnetic disk storage or other magnetic storage devices, or any other medium which can be used to store the desired information and which can be accessed by the device(s) 900. Any such tangible computer-readable media can be part of the device(s) 900.

The device(s) 900 can also include input device(s) 912 and output device(s) 914. In some implementations, the input device(s) 912 can include at least one of a keypad, a cursor control, a touch-sensitive display, a voice input device, a haptic feedback device, or the like. The output device(s) 914 can include at least one of a display, speakers, a haptic output device, printers, etc. These devices are well known in the art and need not be discussed at length here.

As illustrated in FIG. 9, the device(s) 900 can also include one or more wired or wireless transceiver(s) 916. For example, the transceiver(s) 916 can include a Network Interface Card (NIC), a network adapter, a Local Area Network (LAN) adapter, or a physical, virtual, or logical address to connect to the various external devices and/or systems. The transceiver(s) 916 can include any sort of wireless transceivers capable of engaging in wireless communication (e.g., Radio Frequency (RF) communication). The transceiver(s) 916 can also include other wireless modems, such as a modem for engaging in WI-FI™, WiMAX, BLUETOOTH™, or infrared communication. In various examples, the transceiver(s) 916 enable communication between the device(s) 900 and external devices over communication networks (e.g., the first network 106, the second network 112, the third network 116, or a combination thereof).

The following clauses describe one or more example embodiments of the present disclosure, either alone or in combination.

1. A method performed by at least one processor, the method including receiving, from a first sensor, first measurements of a first vital sign of an individual determined automatically during a first time period; receiving, from the first sensor, second measurements of the first vital sign of the individual determined automatically during a second time period, the second time period at least partially occurring 24 hours after the first time period and being shorter than the first time period; determining a circadian offset associated with the first measurements and the second measurements; receiving, from a second sensor, third measurements of a second vital sign of the individual determined automatically during the second time period; determining a warning score associated with the second measurements and the third measurements; determining that the circadian offset is outside of a first range and that the warning score is outside of a second range; and in response to determining that the circadian offset is outside of the first range and that the warning score is outside of the second range, causing a user device to output a user interface indicating an alert associated with the first individual.

2. The method of clause 1, the circadian offset being a first circadian offset and the warning score being a first warning score, the method further including: determining that a second circadian offset of a second individual is within the first range and that a second warning score of the second individual is within the second range, wherein causing the user device to output the user interface includes causing the user interface to display an indication that the second individual is associated with a non-alert status along with the alert corresponding to the first individual.

3. The method of clause 1 or 2, wherein determining the warning score includes: determining a linear line-of-best-fit of the second measurements over the second time period; determining a correction by multiplying a slope of the linear line-of-best-fit by half of the second time period; determining a corrected average by adding the average and the correction; and calculating the warning score based on the corrected average.

4. The method of any one of clauses 1 to 3, further including: in response to determining the warning score, causing the user device to output an indication of the warning score; and in response to determining the circadian offset, causing the user device to output an indication of the circadian offset with the warning score.

5. A system, including: at least one processor in communication with a biological sensor and a transceiver; and memory storing instructions that, when executed by the at least one processor, cause the at least one processor to perform operations including: receiving, from a first sensor, first measurements of a first biological condition of an individual determined automatically during a time period; receiving, from a second sensor, second measurements of a second biological condition of the individual determined automatically during the time period; determining a first average of the first measurements; determining a second average of the second measurements; determining a warning score associated with the first average and the second average; determining that the warning score is outside of a predetermined range; and in response to determining that the warning score is outside of the predetermined range, causing a clinical device to output an alert associated with the individual.

6. The system of clause 5, the time period being a first time period, the predetermined range being a first predetermined range, wherein the operations further include: receiving, from the first sensor, third measurements of the first biological condition of the individual determined during a second time period, the second time period at least partially occurring 24 hours prior to the first time period and being longer than the first time period; determining a third average of the third measurements; determining a circadian offset based on the first average and the third average; and determining that the circadian offset is outside of a second predetermined range, and wherein causing the clinical device to output the alert associated with the individual is performed in response to determining that the circadian offset is outside of the second predetermined range.

7. The system of clause 5 or 6, wherein the time period is between half of an hour and eight hours.

8. The system of any one of clauses 5 to 7, wherein determining the first average includes: determining a line-of-best-fit for the first measurements; determining the first average based on the line-of-best-fit.

9. The system of clause 8 wherein determining the first average based on the line-of-best fit includes: determining a raw average of the first measurements; determining a correction by multiplying a slope of the line-of-best-fit by half of the second time period; and determining a corrected average by adding the raw average to the correction.

10. The system of any one of clauses 5 to 9, wherein causing the clinical device to output the alert includes transmitting, to the clinical device, an instruction to output a user interface indicating the alert.

11. The system of clause 10, wherein the instruction is to output the alert as at least one of an auditory signal, a haptic signal, or a visual signal.

12. The system of any one of clauses 5 to 11, the individual being a first individual, the warning score being a first circadian offset, the operations further including: determining a second warning score associated with a second individual is within the predetermined range, wherein causing the clinical device to output the alert associated with the first individual includes causing the clinical device to output the alert associated with the first individual with an indication that the second individual has a non-alert status.

13. A system, including: at least one processor; and at least one memory storing instructions that, when executed by the at least one processor, cause the processor to perform operations including: receiving, from at least one sensor, first measurements of a biological condition of an individual determined during a first time period; determining a first average of the first measurements; receiving, from the at least one sensor, second measurements of the biological condition of the individual determined during a second time period, the second time period at least partially occurring 24 hours after the first time period and being shorter than the first time period; determining a second average of the second measurements; determining a circadian offset based on the first average and the second average; determining that the circadian offset is outside of a predetermined range; and in response to determining that the circadian offset is outside of the predetermined range, causing a clinical device to output an alert associated with the individual.

14. The system of clause 13, the biological being a first biological condition, the predetermined range being a first predetermined range, wherein the operations further include: receiving, from the at least one sensor, third measurements of a second biological condition of the individual determined during the second time period; determining a third average of the third measurements; determining a warning score based on the second average and the third average; and determining that the warning score is outside of a second predetermined range, and wherein causing the clinical device to output the alert is performed in response to determining that the warning score is outside of the second predetermined range.

15. The system of clause 13 or 14, wherein the first time period is between one hour and eight hours, and wherein the second time period is between half of an hour and four hours.

16. The system of any one of clauses 13 to 15, wherein determining the second average includes: determining a line-of-best-fit for the second measurements; determining the second average based on the line-of-best-fit.

17. The system of clause 16, wherein determining the second average based on the line-of-best fit includes: determining a raw average of the second measurements; determining a correction by multiplying a slope of the line-of-best-fit by half of the second time period; and determining a corrected average by adding the raw average to the correction.

18. The system of any one of clauses 13 to 17, wherein causing the clinical device to output the alert includes transmitting, to the clinical device, an instruction to output a user interface indicating the alert.

19. The system of clause 18, wherein the instruction is to output the alert as at least one of an auditory signal, a haptic signal, or a visual signal.

20. The system of any one of clauses 13 to 19, the individual being a first individual, the circadian offset being a first circadian offset, the operations further including: determining a second circadian offset associated with a second individual is within the predetermined range, wherein causing the clinical device to output the alert associated with the first individual includes causing the clinical device to output the alert associated with the first individual with an indication that the second individual has a non-alert status.

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

As used herein, the term "based on" can be used synonymously with "based, at least in part, on" and "based at least partly on."

As used herein, the terms "comprises/comprising/comprised" and "includes/including/included," and their equivalents, can be used interchangeably. An apparatus, system, or method that "comprises A, B, and C" includes A, B, and C, but also can include other components (e.g., D) as well. That is, the apparatus, system, or method is not limited to components A, B, and C.

Although the subject matter has been described in language specific to structural features and/or methodological acts, it is to be understood that the subject matter defined in the appended claims is not necessarily limited to the specific features or acts described.

The invention claimed is:

1. A system, comprising:
    at least one processor; and
    at least one memory storing instructions that, when executed by the at least one processor, cause the processor to perform operations comprising:
        receiving, from at least one sensor, first measurements of a biological condition of an individual determined during a first time period;
        determining a first average of the first measurements;
        receiving, from the at least one sensor, second measurements of the biological condition of the individual determined during a second time period, the second time period at least partially occurring 24 hours after the first time period and being shorter than the first time period;
        determining a second average of the second measurements;
        determining a circadian offset based on a difference between the first average and the second average;
        determining whether the circadian offset is outside of a predetermined range; and
        based on determining that the circadian offset is outside of the predetermined range, causing a clinical device to output an alert associated with the individual.

2. The system of claim 1, the biological being a first biological condition, the predetermined range being a first predetermined range, wherein the operations further comprise:
    receiving, from the at least one sensor, third measurements of a second biological condition of the individual determined during the second time period;
    determining a third average of the third measurements;
    determining a warning score based on the second average and the third average; and
    determining whether the warning score is outside of a second predetermined range, and
    wherein causing the clinical device to output the alert is performed based on determining that the warning score is outside of the second predetermined range.

3. The system of claim 1, wherein the first time period is between one hour and eight hours, and wherein the second time period is between half of an hour and four hours.

4. The system of claim 1, wherein determining the second average comprises:
    determining a line-of-best-fit for the second measurements;
    determining the second average based on the line-of-best-fit.

5. The system of claim 4, wherein determining the second average based on the line-of-best fit comprises:
    determining a raw average of the second measurements;
    determining a correction by multiplying a slope of the line-of-best-fit by half of the second time period; and
    determining a corrected average by adding the raw average to the correction.

6. The system of claim 1, wherein causing the clinical device to output the alert comprises transmitting, to the clinical device, an instruction to output a user interface indicating the alert.

7. The system of claim 6, wherein the instruction is to output the alert as at least one of an auditory signal, a haptic signal, or a visual signal.

8. The system of claim 1, the individual being a first individual, the circadian offset being a first circadian offset, the operations further comprising:
    determining a second circadian offset associated with a second individual is within the predetermined range;
    wherein causing the clinical device to output the alert associated with the first individual comprises causing the clinical device to output the alert associated with the first individual with an indication that the second individual has a non-alert status.

9. The system of claim 1, wherein the system comprises the at least one sensor, the at least one sensor comprising at least one automated sensor.

10. The system of claim 1, wherein the system comprises the clinical device.

11. A method, comprising:
    receiving, from at least one sensor, first measurements of a biological condition of an individual determined during a first time period;
    determining a first average of the first measurements;
    receiving, from the at least one sensor, second measurements of the biological condition of the individual determined during a second time period,
        at least part of the second time period occurring 24 hours after the first time period, and
        the second time period being shorter than the first time period;
    determining a second average of the second measurements;
    determining a circadian offset based on a difference between the first average and the second average;
    determining whether the circadian offset is outside of a predetermined range; and
    based on determining that the circadian offset is outside of the predetermined range, causing a clinical device to output an alert associated with the individual.

12. The method of claim 11, the biological being a first biological condition, the predetermined range being a first predetermined range, wherein the method further comprises:
    receiving, from the at least one sensor, third measurements of a second biological condition of the individual determined during the second time period;
    determining a third average of the third measurements;
    determining a warning score based on the second average and the third average; and
    determining whether the warning score is outside of a second predetermined range,
        wherein the clinical device is caused to output the alert based on determining that the warning score is outside of the second predetermined range.

13. The method of claim 11, wherein the first time period is between one hour and eight hours, and
    wherein the second time period is between half of an hour and four hours.

14. The method of claim 11, wherein determining the second average comprises:
    determining a line-of-best-fit for the second measurements; and
    determining the second average based on the line-of-best-fit.

15. The method of claim 14, wherein determining the second average based on the line-of-best fit comprises:
    determining a raw average of the second measurements;
    determining a correction by multiplying a slope of the line-of-best-fit by half of the second time period; and
    determining a corrected average by adding the raw average to the correction.

16. The method of claim 11, wherein causing the clinical device to output the alert comprises transmitting, to the clinical device, an instruction to output a user interface indicating the alert.

17. The method of claim 16, wherein the instruction is to output the alert as at least one of an auditory signal, a haptic signal, or a visual signal.

18. The method of claim 11, the individual being a first individual, the circadian offset being a first circadian offset, the method further comprising:
    determining a second circadian offset associated with a second individual is within the predetermined range;
    wherein causing the clinical device to output the alert associated with the first individual comprises causing the clinical device to output the alert associated with the first individual with an indication that the second individual has a non-alert status.

* * * * *